(12) United States Patent
Lavoie et al.

(10) Patent No.: US 6,699,839 B1
(45) Date of Patent: Mar. 2, 2004

(54) **LANTIBIOTIC FROM *STREPTOCOCCUS MUTANS*, METHOD OF PRODUCTION AND USE THEREOF**

(75) Inventors: Marc Lavoie, Loretteville (CA); Marilaine Mota-Meira, Loretteville (CA); Christophe Lacroix, Sillery (CA); Gisèle Lapointe, Ste-Foy (CA)

(73) Assignee: Universite Laval, Quebec (CA)

( * ) Notice: Subject to any disclaimer, the term of this patent is extended or adjusted under 35 U.S.C. 154(b) by 613 days.

(21) Appl. No.: 09/691,150

(22) Filed: Oct. 19, 2000

Related U.S. Application Data (62) Division of application No. 08/924,952, filed on Sep. 8, 1997, now Pat. No. 6,218,362.

(51) Int. Cl.$^7$ ............................................. A61K 38/00
(52) U.S. Cl. ......................................................... 514/13
(58) Field of Search ...................... 514/13, 2; 530/300, 530/350, 326

(56) References Cited

U.S. PATENT DOCUMENTS

| | | |
|---|---|---|
| 4,693,888 A | 9/1987 | Miyahara et al. |
| 5,173,297 A | 12/1992 | Vedamuthu et al. |
| 5,231,013 A | 7/1993 | Jung et al. |
| 5,573,797 A | 11/1996 | Wilhoit |
| 5,594,103 A | 1/1997 | De Vos et al. |
| 5,607,672 A | 3/1997 | Hillman |
| 5,650,320 A | 7/1997 | Caufield et al. |

FOREIGN PATENT DOCUMENTS

| | | |
|---|---|---|
| CA | 1277617 | 12/1990 |
| CA | 1336896 | 9/1995 |
| WO | WO 93/11738 | 6/1993 |
| WO | WO 94/04682 | 3/1994 |
| WO | WO 95/01154 | 1/1995 |

OTHER PUBLICATIONS

Bierbaum et al., 1993, Zentralbl. Bakteriol. 278:1–22.
Chan et al., 1996, Appl. Environ. Microbiol. 62:2966–2969.
Chikindas et al., 1995, Antimicrob. Agents Chemother. 39:2656–2660.
Delisle, A.L., 1986, Microbios 46:21–28.
Delisle, A.L., 1975, Antimicrob. Agents Chemother. 8:707–712.
Fukushima et al., 1985, Arch. Oral Biol. 30:229–234.
Gilmore et al., 1994, J. Bacteriol. 176:7335–7344.
Gross et al., 1971, J. Am. Chem. Soc. 93:4634–4635.
Hamada et al, 1975, Arch. Oral Biol. 20:641–648.
Hamada et al., 1986, Zentralbl. Bakteriol. Hyg. A. 261:287–298.
Harlander, S.K., 1993, Bacteriocins of Lactic Acid Bacteria, Academic Press: 233–47.
Hillman et al., 1984, Infect. Immun. 44:141–144.
Hurst, A., 1966, J. Gen. Microbiol. 45:503–513.
Jack et al., 1995, Microbiol. Rev. 59:171–200.
Jack et al., 1995, Trends Biotechnol. 13:269–278.
Jack et al., 1994, Eur J Biochem 220:455–462.
Jack et al., 1991, in: Nisin and Novel Lantibiotics, Jung et al., Eds., ESCOM Science, Leiden, pp. 171–179.
Jung, G., 1991, in: Nisin and Novel Lantibiotics, Jung et al., Eds., ESCOM Science, Leiden, pp. 1–34.
Kelstrup et al., 1977, J. Biol. 5:99–106.
Kurita et al., 1988, J. Gen. Microbiol. 134:213–220.
Liu et al., 1993, Appl. Environ. Microbiol. 59:648–651.
Loyola–Rodriguez et al., 1992, J. Gen. Microbiol. 138:269–274.
Meyer et al., 1994, Anal. Biochem. 223:185–190.
Morency et al., 1995, Can. J. Microbiol. 41:826–831.
Mota–Meira et al., 1996, FEMS Symposium on lactic acid bacteria, The Netherlands.
Nes et al., 1996, Antonie van Leeuwenhoek 69:89–97.
Novák et al., 1993, ASM meeting Abstr. No. A–44, p. 8.
Novák et al., 1994, J. Bacteriol 176:4316–4320.
Novák et al., 1996, Anal. Biochem. 236:358–360.
Ottenwälder et al., 1995, Appl. Environ. Microbiol. 61:3894–3903.
Parrot et al., 1989, Can. J. Microbiol. 35:366–372.
Parrot et al., 1992, Congrès de l'AMQ, p. 22.
Parrot et al., 1990, Can. J. Microbiol. 36:123–130.
Paul et al., 1975, Infect. Immun. 12:1375–1385.
Peschel et al., 1996, J. Bacteriol. 178:531–536.
Peschel et al., 1997, Mol Gen Genet 254:312–318.
Ray, B., 1992, in: Food Biopreservative of Microbial Origin, Ray et al., Eds, CRC Press Inc., Boca Raton IL: 207–264.
Rogers, A.H., 1972, Appl. Microbiol. 24:294–295.
Rollema et al., 1995, Appl. Environ. Microbiol. 61:2873–2878.
Ross et al., 1993, Appl. Environ. Microbiol. 59:2014–2021.
Sahl et al., 1985, Antimicrob. Agents Chemother. 27:836–840.
Schnell et al., 1992, Eur. J. Biochem. 204:57–68.
Schnell et al., 1988, Nature 333:276–278.
Schnell et al., 1989, FEMS Microbiol. Lett. 58:263–268.
Snyder, L.R., 1978, Chromatogr. Sci. 16:223–234.
Takada et al., 1984, Infect. Immun. 44:370–378.
Mota–Meira et al., 1997, FEBS Letters 410:275–279.
Daeschel Mark A., 1992, Bacteriocin of Lactic Acid Bacteria:63–91.

*Primary Examiner*—Karen Cochrane Carlson
*Assistant Examiner*—Sheridan Snedden
(74) *Attorney, Agent, or Firm*—Goudreau Gage Dubuc; Alain M. Leclerc; Julie Gauvreau (57) ABSTRACT

Mutacin are bactericidal substances of proteinaceous natures produced by *Streptococcus mutans*. Lantibiotics are antibacterial substances containing posttranslationnally modified amino acids such as lanthionine. The present invention teaches a simple method of purifying mutacin B-Ny266 from *Streptococcus mutans* strain Ny266 to homogeneity. The present invention further teaches the primary amino acid sequence of mutacin B-Ny266 as well as its proposed modified structure. Further, the present invention teaches compositions comprising mutacin B-Ny266 as well as methods for the treatment and/or prophylaxy of bacterial infections comprising an administration of a suitable dose of composition comprising mutacin B-Ny266.

15 Claims, 1 Drawing Sheet

MUTACIN B-Ny266

EPIDERMIN

GALLIDERMIN

FIG. 1

LANTIBIOTIC FROM *STREPTOCOCCUS MUTANS*, METHOD OF PRODUCTION AND USE THEREOF

This application is a division of Ser. No. 08/924,952 filed Sep. 8, 1997 now U.S. Pat. No. 6,218,362.

FIELD OF THE INVENTION

The present invention relates to a novel antibiotic produced by *streptococcus mutans*, salts thereof, pharmaceutical compositions containing same, and to methods for the production and extraction thereof.

BACKGROUND OF THE INVENTION

Bacteriocins produced by Gram-positive bacteria can be defined as inhibitory substances having a bactericidal mode of action and an essential protein moiety (Jack et al., 1995, Microbiol. Rev. 59:171–200). Bacteriocins produced by *Streptococcus mutans* were termed mutacins by Hamada and Ooshima (Hamada et al, 1975, Arch. Oral Biol. 20:641–648). Although there are many reports which show that *S. mutans* produces inhibitory substances, only a few such inhibitors have been isolated and characterized as mutacins (Chikindas et al., 1995, Antimicrob. Agents Chemother. 39:2656–2660; Delisle, 1986, Microbios 46:21–28; Fukushima et al., 1985, Arch. Oral Biol. 30:229–234; Hamada et al., 1986, Zentralbl. Bakteriol. Hyg. A. 261:287–298; Hillman et al., 1984, Infect. Immun. 44:141–144; Kurita et al., 1988, J. Gen. Microbiol. 134:213–220; Loyola-Rodriguez et al., 1992, J. Gen. Microbiol. 138:269–274; Novak et al., 1994, J. Bacteriol. 176:4316–4320; Novák et al., 1996, Anal. Biochem. 236:358–360; Paul et al., 1975, Infect. Immun. 12:1375–1385; Takada et al., 1984, Infect. Immun. 44:370–378). The well studied mutacins include: RM-10 (Fukushima et al., 1985, Arch. Oral Biol. 30:229–234), C3603 (Takada et al., 1984, Infect. Immun. 44:370–378), JH 1000 (Hillman et al., 1984, Infect. Immun. 44:141–144), GS-5 (Paul et al., 1975, Infect. Immun. 12:1375–1385), MT 3791 and MT 6223 (Hamada et al., 1986, Zentralbl. Bakteriol. Hyg. A. 261:287–298;Loyola-Rodriguez et al., 1992, J. Gen. Microbiol. 138:269–274), mutacin-b (Delisle, 1986, Microbios 46:21–28), mutalipocins (Kurita et al., 1988, J. Gen. Microbiol. 134:213–220) and J-T8 (Chikindas et al., 1995, Antimicrob. Agents Chemother. 39:2656–2660; Novák et al., 1994, J. Bacteriol. 176:4316–4320;Novák et al., 1996, Anal. Biochem. 236:358–360).

A preliminary classification of mutacins has been published previously (Morency et al., 1995, Can. J. Microbiol. 41:826–831), but a definitive classification will have to await the complete chemical characterization of these substances. Among the known mutacins, only T8, which belongs to group J (Morency et al., 1995, Can. J. Microbiol. 41:826–831), was identified as a lantibiotic and its first 8 N-terminal amino acid residues were determined by Novák et al. (Novák et al., 1994, J. Bacteriol. 176:4316–4320). Lantibiotics are defined as bacterium-derived ribosomally synthesized lanthionine-containing peptides with antibiotic activity (Jack et al., 1995, Microbiol. Rev. 59:171–200; Bierbaum et al., 1993, Zentralbl. Bakteriol. 278:1–22;Jack et al., 1995, Trends Biotechnol. 13:269–278). They generally contain unsaturated amino acids like 2,3-didehydroalanine (dhA or U) (2)-2,3-didehydrobutyrine (dhB or O), and 2-aminobutyric acid (Abu). The lantibiotics are divided into two types (Jack et al., 1995, Microbiol. Rev. 59:171–200; Bierbaum et al., 1993, Zentralbl. Bakteriol. 278:1–22; Jack et al., 1995, Trends Biotechnol. 13:269–278; Jung, 1991, in: Nisin and Novel Lantibiotics., Jung et al., eds., pp. 1–34. ESCOM Science, Leiden). Type A comprises screw-shaped, amphipathic molecules with molecular masses between 2151 and 4635 Da and with 2 to 7 net positive charges. Type B consists of more globular molecules with molecular masses between 1825 and 2042 Da and with either no net charge or a net negative charge. They usually contain a higher proportion of modified amino acid residues than type A.

Only four streptococcal strains were shown to produce a lantibiotic: Streptococcus pyogenes producing streptococcin A-FF22 (Jack et al., 1994, Eur J Biochem 220:455–462), *Streptococcus salivarius* producing salivaricin A (Ross et al., 1993, Appl. Environ. Microbiol. 59:2014–2021), *Streptococcus mutans* T8 producing mutacin J-T8 (Parrot et al., 1990, Can. J. Microbiol. 36:123–130; Parrot et al., 1992, Congrès de l'AMQ, p. 22; Novak et al., 1993, ASM meeting Abstr. No. A-44, p. 8; Novak et al., 1994, J. Bacteriol 196:4316–4320).

*Streptococcus mutans* strain B-Ny266 has been previously shown to inhibit 98% of the *S. mutans* strains tested (Morency et al., 1995, Can. J. Microbiol. 41:826–831) and all tested Gram-positive bacteria including *Listeria monocyto genes, Clostridium sporogenes, Mycobacterium phleï, Staphylococcus aureus, Enterococcus faecalis* and *Bacillus subtilis* (Parrot et al., 1990, Can. J. Microbiol. 36:123–130). A preliminary characterization of the antibacterial effect of this strain permitted to hypothesize that at least one mutacin was responsible therefor. However, the mutacin(s) of B-Ny266 has yet to be purified. Furthermore, it remains to be determined whether the wide antibacterial activity associated with strain B-Ny266 is attributable to a single proteinaceous substance or shared by two or more proteinaceous substances therein (Morency et al., 1995, Can. J. Microbiol. 41:826–831; and references therein). It follows, that the determination of the amino sequence of the antibacterial substance(s) present in B-Ny266 had yet to be carried out.

There thus remains a need to purify to homogeneity the bacterial substance(s) carrying the demonstrated antibacterial activity present in *S. mutans* strain B-Ny266. There further remains a need to identify the amino acid sequence of this substance.

The present invention seeks to meet these and other needs.

The present description refers to a number of documents, the content of which is herein incorporated by reference.

SUMMARY OF THE INVENTION

The invention concerns the purification to homogeneity of the proteinaceous substance having bactericidal activity produced by *Streptococcus Mutans* B-Ny266. More particularly, the present invention concerns the purification to homogeneity of a lantibiotic type A produced by *Streptococcus mutans* B-Ny266, hereinafter termed mutacin B-Ny266.

The invention also relates to the amino acid sequence of mutacin B-Ny266. More particularly, the invention relates to the primary amino acids sequence of pro-B-Ny266 the precursor protein of mutacin B-Ny266: F-K-S-W-S-F-C-T-P-G-C-A-K-T-G-S-F-N-S-Y-C-C (SEQ ID NO:1). Further, the present invention relates to pro-B-Ny266 sequence being posttranslationnally modified to yield the proposed sequence: F-K-<u>A</u>-W-U-F-<u>A</u>-<u>Abu</u>-P-G-<u>A</u>-A-K-O-G-<u>A</u>-F-N-<u>U</u>-Y-<u>A</u> (SEQ ID NO:4; underlined residues participate in lanthionine or b-methyllanthionine bridges).

The present invention further relates to methods of purifying to homogeneity Mutacin B-Ny266 from *S. mutants* strain B-Ny266. Further, the invention relates to methods of purifying to homogeneity type A mutacins from *S. mutants* being close relatives to mutacin B-Ny266. More particularly, the invention relates to methods for the preparation of mutacin B-Ny266 and pharmaceutically acceptable salts thereof comprising cultivating microorganisms capable of expressing mutacin B-Ny266, preferably *S. mutants* B-Ny266, under condition whereby mutacin B-Ny266 is expressed, isolated, secreted and extracted from cell pellets of the strain expressing B-Ny266 in the culture medium, and if desired, converting the isolated mutacin B-Ny266 to a pharmaceutically acceptable salt thereof, *S. Mutans* B-Ny266 has been deposited at the American Type Culture Collection (ATCC, 12301 Parklawn Drive, Rockville, Md.) on Aug. 22, 1997 and granted the accession number ATCC 202022.

The invention in addition relates to pharmaceutical compositions comprising mutacin B-Ny266 and pharmaceutically acceptable carriers or excipients. Further, the invention relates to pharmaceutical compositions comprising as active ingredient, mutacin B-Ny266 or a pharmaceutically acceptable salt thereof, and associated with a pharmaceutically acceptable carrier or excipient.

The present invention therefore further relates to a purified preparation of mutacin B-Ny266. More particularly, the invention relates mutacin B-Ny266 purified to more than 80% homogeneity more preferably to more than 90% homogeneity and in a further preferred embodiment to mutacin B-Ny266 purified to approximately 99% homogeneity.

The applicant was the first to purify a *Streptococcus mutans* mutacin to homogeneity. More particularly, the applicant is the first to purify mutacin B-Ny266 to homogeneity and to determine its complete amino acids sequence. The applicant is therefore the first to obtain a complete amino acids sequence of a lantibiotic produced by *S. mutants*.

Before the present invention, it was unclear whether *S. mutants* strain B-Ny266 antibacterial activity was determined by a single proteinaceous substance. Further, prior to the present invention, in view of the difficulty in purifying to homogeneity mature, modified peptides such as lantibiotic, mutacin B-Ny266 had yet to be obtained in a pure form. The applicant is thus the first to provide antibacterial pharmaceutical compositions comprising mutacin B-Ny266.

The amino acid sequence of mutacin B-Ny266 completely differs from that of streptococcin A-FF22, salivariucin A, and mutacin J-T8. It is however somewhat apparented to the sequence of epidermin and gallidermin although it differs therefrom by five amino acid residues.

It is noteworthy that gallidermin and epidermin only differ from each other by one amino acid while their antibacterial activity have distinguishing features. Contrary to epidermin (Peschel et al., 1996, J. Bacteriol. 178:531–536; Peschel et al., 1997, Mol Gen Genet 254:312–318; Schnell et al., 1988, Nature 333:276–278; Schnell et al., 1992, Eur. J. Biochem. 204:57–68) and like gallidermin (Schnell et al.,1989, FEMS Microbiol. Lett. 58:263–268), the genes coding for mutacin B-Ny266 are located on the chromosome (Mota-Meira et al., 1996, FEMS Symposium on lactic acid bacteria, The Netherlands).

Mutacin B-Ny266 has a molecular mass of 2270 Da while epidermin and gallidermin have a molecular mass of 2164 Da (Nes et al., 1996, Antonie van Leeuwenhoek 69:89–97). Apart from subtilin, it is the only lantibiotic of type A with a net charge of +2 (Nes et al., 1996, Antonie van Leeuwenhoek 69:89–97). It is the only type A lantibiotic with a phenylalanine N-terminal residue (Nes et al., 1996, Antonie van Leeuwenhoek 69:89–97) and it contains 3 phenylalanine residues like cytolysin LS from *Enterococcus faecalis* (Gillmore et al., 1994, J. Bacteriol. 176:7335–7344) as opposed to none in nisin (Gross et al., 1971, J. Am. Chem. Soc. 93:4634–4635) and two in epidermin/gallidermin.

The above-mentioned features clearly indicate that mutacin B-Ny266 is unique among lantibiotics.

In accordance with the present invention, there is therefore provided, an isolated mutacin B-Ny266 polypeptide comprising the amino acid sequence of pro-B-Ny266: F-K-S-W-S-F-C-T-P-G-C-A-K-T-G-S-F-N-S-Y-C-C (SEQ ID NO:1), or functional derivatives thereof. Additionally, there is also provided an isolated mutacin B-Ny266 polypeptide comprising the amino acid sequence of pro-B-Ny266: F-K-S-W-S-F-C-T-P-G-C-A-K-T-G-S-F-N-S-Y-C-C (SEQ ID NO:1), or functional derivatives thereof, modified into a mature mutacin B-Ny266 polypeptide, comprising amino acid sequence: F-K-A-W-U-F-A-Abu-P-G-A-A-K-O-G-A-F-N-U-Y-A (SEQ ID NO:4), or functional derivatives thereof, wherein underlined residues participate in lanthionine or b-methyllanthionine bridges.

Figure 1:
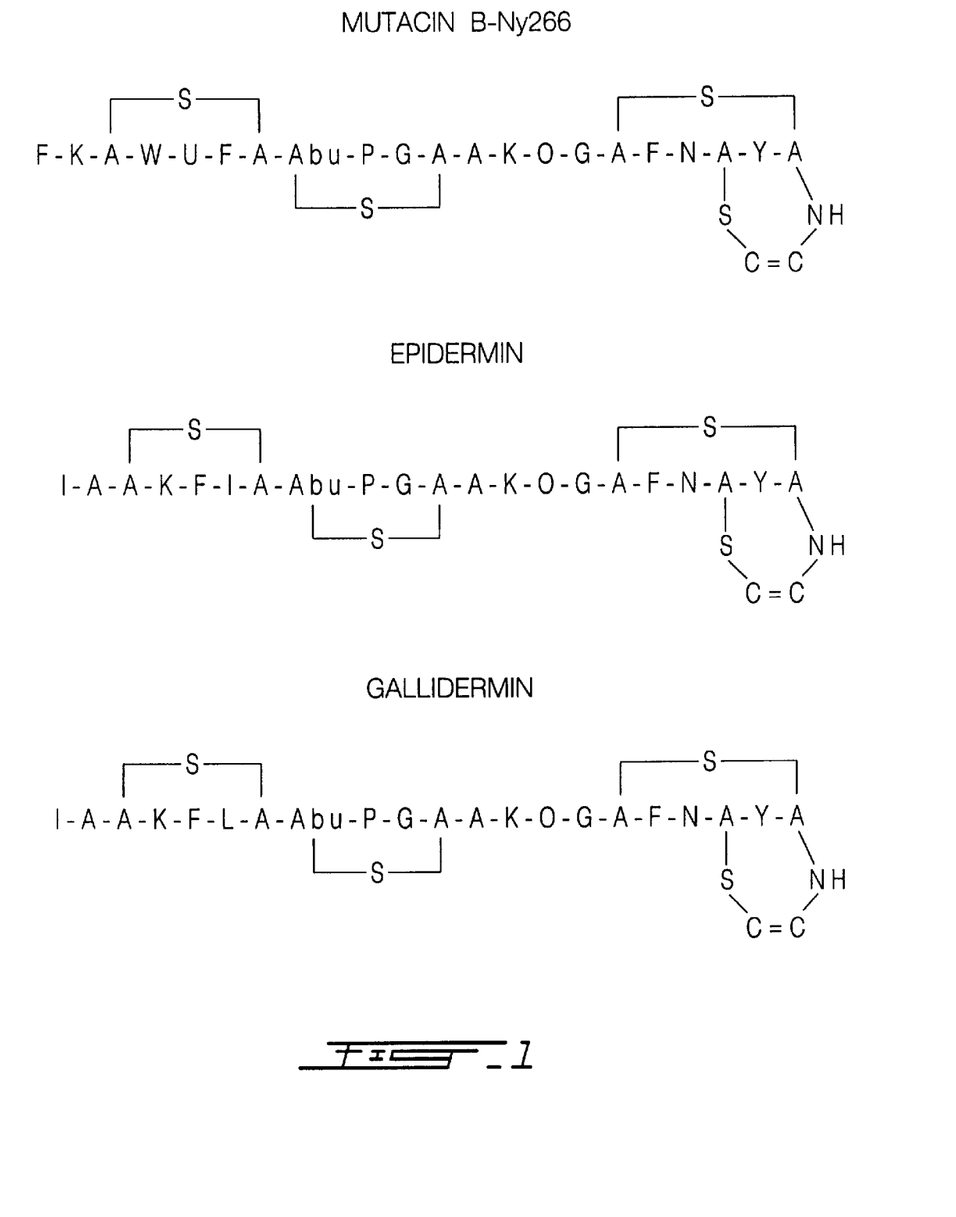
FIG. 1 shows a comparison of the proposed structure of mutacin B-Ny266 with those of Epidermin and Gallidermin.

In accordance with the present invention, there is also provided, a substantially pure preparation of mutacin from *Streptococcus mutans,* having a structure according to FIG. 1.

In accordance with another aspect of the present invention, there is provided, bactericidal and/or bacteriostatic composition comprising an effective amount of the isolated mutacin B-Ny266 polypeptide of the instant invention, and a suitable carrier or excipient. As well there is provided a pharmaceutical composition for the treatment and/or prophylaxis of bacterial strains susceptible to mutacin B-Ny266, comprising an effective amount of the isolated mutacin B-Ny266 polypeptide of the instant invention, and a pharmaceutically acceptable carrier or excipient.

In accordance with yet another aspect of the present invention, there is provided a method of treating a bacterial infection in an animal, comprising the step of administering a therapeutically effective amount of a pharmaceutical composition according with the instant invention.

As well there is provided a *Streptococcus mutans* strain expressing mutacin B-Ny266 comprising the amino acid sequence of pro-B-Ny266: F-K-S-W-S-F-C-T-P-G-C-A-K-T-G-S-F-N-S-Y-C-C (SEQ ID NO:1), or functional derivatives thereof and a *Streptococcus mutans* strain expressing a mature mutacin B-Ny266 polypeptide, comprising amino acid sequence: F-K-A-W-U-F-A-Abu-P-G-A-A-K-O-G-A-F-N-U-Y-A (SEQ ID NO:4), or functional derivatives thereof, wherein underlined residues participate in lanthionine or b-methyllanthionine bridges.

In accordance with the present invention, there is additionnally provided a method of producing mutacin B-Ny266 having amino acid sequence: F-K-A-W-U-F-A-Abu-P-G-A-A-K-O-G-A-F-N-U-Y-A (SEQ ID NO:4), or functional derivatives thereof, wherein underlined residues participate in lanthionine or b-methyllanthionine bridges, the method comprising the steps of cultivating a *S. Mutans* strain expressing the mutacin, in a suitable culture medium enabling expression, production and maturation thereof, and isolating the mutacin B-Ny266. Also there is provided such a method, wherein said mutacin B-Ny266 is isolated by treating the suitable culture medium with a weak hydrophobic adsorber which adsorbs mutacin B-Ny266, and eluting the mutacin B-Ny266 from the adsorber using a suitable organic solvent.

In accordance with the present invention there is provided a method for inhibiting sensitive bacteria comprising: exposing the bacteria to an inhibitory amount of the mutacin B-Ny266 polypeptides of the instant invention.

As used herein, the designation "functional derivatives" denote a derivative of mutacin B-Ny266 having a related amino acid sequence thereof and retaining mutacin B-Ny266 biological activity. These functional derivatives or equivalents may be natural derivatives of may prepared synthetically. Such derivatives include amino acid sequence having substitutions, deletions, or additions of one or more amino acids, provided that the biological activity of mutacin B-Ny266 is conserved. Generally, the substituting amino acid has chemico-physico properties which are similar to the substituted amino acid. The similar chemico-physico properties include, similarities in charge, bulkiness, hydrophobicity, hydrophylicity and the like.

The term "functional derivatives" is intended to include "fragments", "segments", "variants", "analogs" or "chemical derivatives" of the mutacins of the present invention.

As used herein, "chemical derivatives" meant to cover additional chemical moieties not normally part of the invention. Such moieties could affect the physico-chemical characteristic of the mutacin derivative (i.e. solubility, absorption, half life and the like, decrease of toxicity). Such moieties are examples of described in Remington's Pharmaceutical Sciences (1980). Methods of coupling chemical moieties to a polypeptide are well known in the art.

The term "variant" refers herein to a mutacin having a substantially similar structure and biological activity.

It shall also be understood, that since mutacin B-Ny266 possesses its biological activity after maturation of its original primary amino acid structure, that the person of ordinary skill, will be able to obtain a derivative of mutacin B-Ny266 having an initial primary structure which is different from the primary structure of the pro-mutacin B-Ny266 but can mature into an active mutacin having the identical primary structure as that of mutacin B-Ny266.

The functional derivatives of the present invention can be synthesized chemically or produced through recombinant DNA technology. Non-limiting examples of chemical synthesis include solid phase synthesis using for example a polypeptide synthesis apparatus. Recombinant DNA technology methods are also well known in the art. For example, methods of creating fusion proteins by adding additional amino acid, for example at the amino terminal is considered to be within the scope of what is considered a functional variant.

As used herein, the term "purified" refers to a molecule having been separated from a cellular component. Thus, a "purified protein" has been purified to a cell not found in nature. Herein, the designation "substantially pure" denotes a preparation that is lacking in all other cellular components. As will be taught herein in a preferred embodiment, the substantially pure preparation of mutacin B-Ny266 is 99.9% pure.

While the method of production of mutacin B-Ny266 of the instant invention is demonstrated by growing *Streptococcus mutans* strain B-Ny266 in M17 broth, the cultivation of mutacin B-Ny266 producing microorganisms, such as *S. mutants* can be carried out according to standard methods using conventional culture medium. For instance, *S. mutants* (ATCC 202022) can be cultivated in a rich medium containing meat extracts, yeast extracts and casein and a carbon source. In one preferred embodiment, lactose is used as the carbon source. In another preferred embodiment, the media used is M17 (BDH). Other media, such as a medium containing a suitable nitrogen source, a carbon source, and a hydroxide of an alkaline earth metal, $Ca(OH)_2$ can also be used. To produce large quantities of the bacterial strain, a suitable bioreactor can be operated. In any event, the methods of growing *S. mutans* are well known to the person of ordinary skill. It will be understood by the person of ordinary skill that a synthetic media could in some instances provide advantages, since by being less complex, less undesirable components are present in the media, translating in a simpler purification scheme of the mutacin.

Although in a preferred embodiment, mutacin B-Ny266 is purified to homogeneity by a simple method comprising mutacin B-Ny266 extraction from cell pellets. It has also been found that mutacin B-Ny266 may be readily isolated by the simple, expedient method of isolating the mutacin from the culture medium comprising: treating the culture medium with an adsorber followed by a procedure including the steps of adsorption on a weak hydrophobic resin, desorption with methanol or other suitable organic solvents (non-limiting examples thereof includes isopropanol, ethanol, acetonitrile and the like) and further chromatographic purification stages, e.g., reverse phase-HPLC or chromatography on C18 Sep-Pak (Waters) using, e.g., acetonitrile gradient in 0.11% TFA as eluant. In a preferred embodiment, the hydrophobic resin XAD-7 was used in accordance with the method of purification of the present invention. It will be understood by the person of ordinary skill that other types of hydrophobic chromatography columns can be used in the context of the purification of the present invention. Other hydrophobic columns such as XAD-2, XAD-4, XAD-8, XAD-11, XAD-16, XAD-1180, XAD-2000 could also be used, although XAD-7 has been consistently the most efficacious hydrophobic column used.

As the mutacin B-Ny266 is a strongly basic compound, it will readily form salts by addition of suitable acids, including pharmaceutically acceptable acids according to conventional methods. Physiologically acceptable organic or inorganic acids which can be used for this purpose are, for example, hydrochloric acid, hydrobromic acid, sulphuric acid, benzosulphonic acid, methanesulphonic acid, p-toluenesulphonic acid and cyclohexylsulphamic acid.

In view of its spectrum of antibacterial activity, mutacin B-Ny266 and its acid addition salts are useful for combatting bacteria and for treating bacterial infections. In particular, in view of their activity against important strains of Actinobacilli, Bacillus sp., Clostridium sp., Corynebacteria, Enterococci, *Listeria monocytogenes*, *Mycobacterium phlei*, Neisseria, Propionobactere, Staphylococci, and Streptococci, mutacin B-Ny266 and its acid addition salts are particularly useful in combatting infections caused by Gram-positives bacteria.

Thus according to a further feature of the present invention there are provided pharmaceutical compositions containing, as active ingredient, mutacin B-Ny266 or a pharmaceutically acceptable acid addition salt thereof, in association with one or more inert pharmaceutical carriers and/or excipients. Treatment and prophylaxy of Gram-positive bacterial infections are contemplated as being within the scope of the present invention.

The term pharmaceutical composition as used herein is meant to cover the veterinary field since the mutacin of the invention also finds uses in animal treatment and prophylaxy. Treatment of animals such as cow (mastitis), chicken and the like are within the scope of the present invention.

For pharmaceutical administration, the said polypeptide may be incorporated into preparations in either liquid or solid forms using carriers and excipients conventionally employed in the pharmaceutical art, optionally in combination with further active ingredients. The preparation may, for example, be applied orally, parenterally, enterally or preferably topically. Preferred forms include, for example, solutions, emulsions, gels, sprays, lotions, ointments, creams or powders.

Dosage in pharmaceutical compositions can vary from 0.001 mg/kg to 50 mg/kg of mutacin B-Ny266, in one or more administrations daily, for one or several days. Mutacin B-Ny266 can be administered parenterally by injection or by gradual perfusion over time. It can be administered intravenously, intraperitoneally, intramuscularly, or subcutaneously.

One of ordinary skill can readily determine the amounts of mutacin to be administered. It is apparent that the dosage will be dependent on the particular treatment used. It should also be clear that the dosage should be chosen to display the biological activity without causing adverse effects. It will be understood that age, sex, type of disease, of formulation and other variables known to the person of ordinary skill will affect determination of the dosage to be used.

The pharmaceutically acceptable carriers and excipients are well known in the art. A representative textbook thereon is Remington's Paharamaceutical Sciences, 1980, 16th Ed., Mack Eds.

Advantageously the compositions may be formulated as dosage units, each unit being adapted to supply a fixed dose of active ingredient. The total daily dose may, of course, be varied depending on the subject treated and the particular use of the composition. This can obviously be adapted by the treating professional.

If under certain conditions, it was forseen that it would be beneficial to provide a patient with a longer circulating time and/or slow release of mutacin B-Ny266. Under such conditions, the mutacin B-Ny266 can be trapped in well known delivery molecules such as liposomes, synthetic vesicles, nanoerythrosomes (U.S. Pat. No. 5,653,999) and the like, according to known methods.

Mutacin B-Ny266 and its acid addition salts may also be used as an additive in cosmetic formulations especially those containing collagen in which it would act as a biopreservative and/or stabilizer.

A cosmetic preparation according to the present invention will include mutacin B-Ny266 or an acid addition salt thereof in association with a suitable carrier and/or excipient preferably collagen and optionally other additives suitable for cosmetic preparations such as perfumes and coloring agents. Mutacin B-Ny266 can also be added to an oral composition (i.e. toothpaste or mouthwash) in such types of preparations or compositions mutacin B-Ny266 can be added in an amount of 0.0001 to 10 wt %, preferably 0.001 to 5 wt % and more advandtageously 0.01 to 2 wt %.

In foodstuff protecting compositions in which mutacin B-Ny266 prevents solid or liquid food spoiling (i.e. meats, dowry products, beer, wine and the like) inhibiting or billing bacteria and especially harmful bacteria, mutacin B-Ny266 can be added to the composition in the range of 1.25 mg/Kg to 6.25 mg/Kg ot treated food or 1.25 mg/L to 2.5 mg/L of treated food.

Furthermore, mutacin B-Ny266 or an acid addition salt thereof in association with a suitable carrier and/or excipient can be used as biopreservative agent in foods and in personal hygiene products. Once again, the formulation can be adapted by the person of ordinary skill to suit particular needs. In view of the wide spectrum of bactericidal activity of mutacin B-Ny266, mutacin B-Ny266 or an acid addition salt thereof in association with a suitable carrier and/or excipient could further find uses as anticarries agent (i.e. in toothpaste, mouth wash, and in topical application), disinfectant cleanser (to combat acne for example), selective agent against Gram-positive bacteria in culture media (Ray, 1992, in: Food Biopreservative of Microbial Origin, Ray et al., Eds, CRC Press Inc., Boca Raton Ill.:207–264; Harlanda, 1993, in: Bacteriocins of Lactic Acid Bacteria, Hoover et al., Eds., Acad. Press Inc., San Diego, p. 63–91; Weder et al., Canadian Application 1, 277, 617; and Jung et al., U.S. Pat. No. 5,231,013).

BRIEF DESCRIPTION OF THE DRAWINGS

Having thus generally described the invention, reference will now be made to the accompanying drawing, showing by way of illustration a preferred embodiment thereof, and in which.

Other objects, advantages and features of the present invention will become more apparent upon reading of the following non-restrictive description of preferred embodiments with reference to the accompanying drawing which is exemplary and should not be interpreted as limiting the scope of the present invention.

DESCRIPTION OF THE PREFERRED EMBODIMENT

Our invention presents the first complete sequence of a lantibiotic produced by *Streptococcus mutans*. The inhibitory substance produced by *S. mutans* Ny266 was purified to homogeneity and its proposed modified primary amino acid sequence was determined as: F-K-A-W-U-F-A-Abu-P-G-A-A-K-O-G-A-F-N-U-Y-A-SADC (SEQ ID NO:5; underlined residues participate in lanthionine or b-methyllanthionine bridges). Mutacin B-Ny266 is resistant to a temperature of 100 EC. for 30 min. and to many enzymes. Its activity is destroyed by a treatmeant at 121° C. for 30 min. and by the enzymes alpha-chymotrypsin, papain, pronase E, proteinase K and trypsin. It has a polarity of 8.067 as determined by its elution with 33.3% acetonitrile from a RP-HPLC $C_{18}$ chromatography column. The electrospray mass spectroscopy analysis yielded a molecular mass of 2270.29±0.21 daltons. Mutacin B-Ny266 is a type A lantibiotic. It substantially differs from other type A lantibiotics by its amino acid sequence but is closely related to Epidermin and Gallidermin.

Material and Methods

Mutacin Production

Strain Ny266 of *Streptococcus mutans* was obtained from J. J. van der Hoeven (Dept. of Preventive Dentistry, University of Nijmegen, Nijmegen, The Netherlands). An overnight preculture in M17 broth (BDH Inc., St-Laurent, QC, Canada) was used to inoculate (1%) 1 liter of M17 broth in 2-liter flasks. The cultures were incubated at 37° C. under aerobic conditions in a standing incubator for 24 h.

Determination of Inhibitory Activity

Trypticase Soy Agar (Difco Laboratories, Detroit, Mich.) plates enriched with 0.3% yeast extract were overlaid with 5 ml of melted TSAYE containing a standardized suspension (0.2 ml of an exponentially growing culture at an optical density of 0.1 at 600 nm) of *Micrococcus luteus* ATCC 272 (ATCC, Rockville, Md.). In order to assess the activity of mutacin samples, two-fold dilutions were prepared in 0.11% TFA (Sigma Chemical Co., St. Louis, Mo.) and 5 µl of each dilution deposited on top of the indicator plates. Mutacin activity was expressed in arbitrary units, which correspond to the reciprocal of the last dilution giving a clear inhibition zone against *M. luteus* after 24 h of incubation at 37° C. under aerobic conditions (Parrot et al., 1989, Can. J. Microbiol. 35:366–372).

The specific activity of each preparation was expressed in AU/mg protein. Protein concentrations were determined using the Bio-Rad DC™ protein assay (Bio-Rad, Mississauga, ON, Canada).

Mutacin Extraction and Purification

One liter of a 24-h culture of *S. mutans* Ny266 was centrifuged at 10,000×g for 15 min and the mutacin was extracted from the cell pellet with a mixture of 20 ml HCl (20 mM) and 80 ml of ethanol (70%) at pH 2.0 (adjusted with HCl). The suspensions were heated at 70° C. for 40 min, cooled on ice, and centrifuged at 10,000×g for 15 min. This method was adapted from an extraction technique described by Hurst (Hurst, A., 1966, J. Gen. Microbiol. 45:503–513). The supernatants were evaporated with a rotary evaporator at 37° C. and the concentrates were applied to $C_{18}$ Sep-Pak® cartridges (Waters Corporation, Milford, Mass.) and eluted with a discontinuous gradient of acetonitrile (12%, 18%, 24%, 30%, 33% and 60% acetonitrile in 0.1% TFA). Active fractions (30% and 33% acetonitrile) were then concentrated with a rotary evaporator and dried in a Speed-Vac® concentrator (Model SC110A, Savant Instruments Inc., Farmingdale, N.Y.). The fractions were re-solubilized in 0.11% TFA. They were further purified by RP-HPLC using an analytical $C_{18}$ column (Vitropack Lichrosorb RP™ 18, 5 µm; LKB, Pharmacia Biotech, Uppsala, Sweden). The chromatography was performed on an LKB system (Pharmacia) equipped with two pumps (model 2150), a controller (model 2152), a variable wavelength monitor (model 2151), a Rheodyne M7010 sample injection valve with a 20 µl loop, and a Hewlett-Packard 3396 integrator. Elution was carried out with solvent (A): 0.11% TFA and solvent (B): 60% acetonitrile in 0.1% TFA. The peptides were eluted with a linear gradient of acetonitrile over 44 min at a flow-rate of 1 ml/min and detected at 220 nm. The upper half of the peak showing activity (HPLC I) was concentrated in a Speed-Vac® and re-injected under the same conditions to yield fraction HPLC II and finally the pooled sample consisting of the upper third fraction of this peak from 8 different batches was injected under the same conditions to yield a unique peak (HPLC III) which was used for chemical analyses.

Polarity Calculation

The polarity was calculated from the percentage of acetonitrile at which the substance eluted according to the formula given by Snyder (Snyder, L. R., 1978, Chromatogr. Sci. 16:223–234).

Purity Assessment

The purity of mutacin preparations was assessed by capillary electrophoresis. The samples were injected into a 44-cm capillary (2023 Fused silica capillary, 50 µm I.D.) by hydrodynamic injection on a capillary electrophoresis system (Thermo SP Separation Products, Toronto, ON, Canada). The separation was carried out at 25 kV in sodium phosphate buffer, pH 2.5 and 15% (V/V) acetonitrile, at 30° C. The detection was at 200 nm.

Molecular Mass Determination

Molecular mass was determined for fraction HPLC III by electrospray mass spectroscopy on a VG/Fisons Quatro II electrospray triple quadrupole mass spectrometer (Fison Instruments, Manchester, UK) at the Dept. of Chemistry, University of Waterloo, Waterloo, ON, Canada.

Amino Acid Analysis

Purified mutacin B-Ny266 (fraction HPLC III) was submitted to acid hydrolysis (HCl 6 N, 110° C., 21 h) and o-phthaldialdehyde derivatization according to Sahl et al. (Sahl et al., 1985, Antimicrob. Agents Chemother. 27:836–840). The amino acids were analysed by RP-HPLC chromatography on a Waters HPLC system (Waters Chromatography Division, Milford, Mass.) consisting of a Waters Radial-Pak $C_{18}$ 4-µm column (8 mm×10 cm) at 40° C., two pumps (Waters model 510) and an automatic injector (Waters Model 715). The OPA amino acid derivatives were detected at 425 nm (excitation wavelength 338 nm) on a fluorescence detector (Waters, Model 420). The sum of the Lan and/or BM-Lan residues was determined using D,L-lanthionine (Sigma) as a standard. The number of amino acid residues was calculated from the molar ratio relative to Ala and Asx.

Sequence Determination

Automatic Edman degradation was performed on a Pulsad Liquid Protein sequencer™ (Applied Biosystems model 473, Foster City, Calif.) after ethanethiol treatment as described by Meyer et al. (Meyer et al., 1994, Anal. Biochem. 223:185–190) to permit sequencing of antibiotics. The results were interpreted according to Meyer et al., 1994 (supra).

Protein Sequence Accession Number

The sequence of mutacin B-Ny266 has been deposited in the SWISS-PROT protein sequence database under accession number P80666.

Results

The purification procedure was repeated 8 times. The mean cell yield of the cultures in M17 broth was 0.79±0.04 (mean±standard deviation) g of cell dry weight/L. The specific activity of the cell pellet extracts was 115±43 AU/mg of protein. The specific activity recovered from the supernatants was 22±3 AU/mg of protein. Therefore, only cell pellet extracts were further purified.

The mean values obtained from the 8 runs for the purification and yield for each step are presented in Table 1.

TABLE 1

Mean yield of mutacin B-Ny266 for each purification step[a]

| Purification step | Purification factor | Yield (%) |
| --- | --- | --- |
| Sep-Pak ® | 36 ± 27 | 31 ± 22 |
| HPLC I | 5 ± 3 | 22 ± 2 |
| HPLC II | 3 ± 1 | 49 ± 22 |
| HPLC III | 6 | 31 |
| Total | 3240 ± 81 | 1.0 ± 0.1 |

[a]Values presented are the mean ± standard deviation of eight purifications, except for the third HPLC chromatography, which was performed only once.

On the whole, mutacin B-Ny266 was purified 3240±81 fold with a yield of 1.0±0.1% which correspond to 3.4±0.3 µg per liter of culture. The substance was found to be more than 99.9% pure by capillary electrophoresis. As mutacin B-Ny266 elutes at 33.3% acetonitrile during RP-HPLC, its polarity was calculated to be 8.067.

The electrospray mass spectroscopy analysis yielded a molecular mass of 2270.29±0.21 daltons for the purified mature peptide.

Taking into account the limits of amino acid analysis after acid hydrolysis and OPA derivatization, the amino acid content as determined by acid hydrolysis and Edman degradation are consistent (Table 2). Forty percent are modified amino acids residues.

TABLE 2

Amino acid composition of mutacin B-Ny266

| Amino Acid (one letter code) | Amino acid analysis[a] (Probable number of residues) | Number of Residues per Molecule Edman degradation | Calculated molecular weight (Da) |
|---|---|---|---|
| Ala (A) | 1.2 (1) | 1 | 71.08 |
| Asx (N, D) | 0.8 (1) | 1 (N) | 114.10 |
| Gly (G) | 1.5 (1–2) | 2 | 114.10 |
| Lys (K) | 2.5 (2–3) | 2 | 256.35 |
| Phe (F) | 2.9 (3) | 3 | 441.53 |
| Tyr (Y) | 0.7 (1) | 1 | 163.18 |
| Lan/BM-Lan[b] | 2.7 (3) | 3 (2 Lan + 1BM-Lan) | 530.65 |
| dhA (U) | 0[c] | 2 | 138.13 |
| dhB (O) | 0[c] | 1 | 83.09 |
| Pro (P) | NQ[d] | 1 | 97.12 |
| Trp (W) | 0[c] | 1 | 186.21 |
|  |  |  | 2195.54 |
|  |  | +1H (N-terminal) | 1.01 |
|  |  |  | 2196.55 |

[a]The number of amino acid residues was calculated from the molar ratio relative to Ala and Asx after OPA derivatization
[b]Lan = Lanthionine
BM-Lan = b-methyllanthionine
[c]dhA, dhB and Trp are acid labile and are not detected by the method used
[d]NQ, not quantified by OPA derivatization

TABLE 3

Sensitivity to mutacin B-Ny266 and nisin of multi-drug resistant staphylococci clinical isolates

| Isolate | Antibiotic resistant[1] | Nisaplin ® titer[2] | Mutacin B-Ny266 titer[2] |
|---|---|---|---|
| Micrococcus luteus ATCC 272 (control) | None | 64 | 64 |
| Staphylococcus haemolyticus 2344 | AM-K-S-CF-E-P-Cl-TE | 4 | 16 |
| Staphylococcus epidermidis 1656 | AM-K-S-CF-E-P-Cl-TE | 16 | 16 |
| Staphylococcus epidermidis 3176 | AM-GM-K-CF-E-P-Cl- | 32 | 16 |

[1]AM = Ampicillin; GM = Gentamycin; K = Kanamycin; S = Streptomycin; CF = Cephalothin; E = Erythromycin; P = Penicillin; Cl = Colistin; TE = Tetracyclin
[2]The titer correspond to the highest dilution producing an inhibitory zone on a lawn of the tested strain.

Edman degradation after treatment with alkaline ethanethiol revealed 21 residues with the following sequence:

F-K-(SEC+DSER)-W-SEC-F-(SEC+DSER)-BMSEC-P-G-(SEC+DSER)-A-K-BMSEC-G-SEC-F-N-SEC-Y-SEC

The sample was sequenced with an initial yield of 1060 pmoles and a repetitive yield of 87.2%. The level of confidence was higher than 99%.

Discussion

Mutacins have always been difficult to obtain from liquid cultures (Hamada et al, 1975, Arch. Oral Biol. 20:641–648; Parrot et al., 1990, Can. J. Microbiol. 36:123–130; Delisle, 1975, Antimicrob. Agents Chemother. 8:707–712; Kelstrup et al., 1977, J. Biol. 5:99–106; Rogers, 1972, Appl. Microbiol. 24:294–295). Novák et al. (Novák et al., 1994, J. Bacteriol. 176:4316–4320) recently obtained good production of mutacin J-T8 in a chemically defined medium enriched with yeast extract and trypticase soy broth. As seen above, a good production of mutacin B-Ny266 was obtained from the commercially available medium M17 (BDH). Furthermore, a simple technique permitting the extraction of the mutacin activity from cell pellets has been described as well as, the first ever complete amino acid sequence of a mutacin.

Although the specific activity recovered from cell pellets is higher than that recovered from supernatants of bacterial cultures, the total amount of activity in the supernatants was calculated to be, on average, six times that of the cell extracts. Actually, 40% of this activity can be recovered, but with a lower purity than from the cell extract (data not shown). The potential is there to purify larger quantities of mutacin B-Ny266 from these supernatants. The method of extraction from cells pellets, displays some variability from one extraction to another. Nevertheless, it permitted the purification of the antibiotic B-Ny266 using only hydrophobicity chromatography. No impurities interfered with the determination of molecular mass and the amino acid sequencing. Furthermore, capillary electrophoresis indicated that the substance was more than 99.9% pure. The method of extraction from the cell pellets is therefore rapid, simple and efficacious as it provides a 99.9% pure mutacin B-Ny266 preparation.

During the first sequencing attempt, Edman degradation was blocked at the first dhA (residue 5), the Trp4 was barely detectable, and a blank was obtained in the third position (preliminary results not shown). The ethanethiol treatment described by Meyer et al. (1994, supra) permitted the complete (residue 22 excepted) sequencing of the molecule. These results thus confirm the conclusions of Meyer et al. (1994, supra) on the usefulness of this method for the automatic sequencing of lantibiotics.

The results obtained from amino acid analysis and Edman degradation are consistent (Table 2), taking into account the residues that could not be identified by amino acid analysis. DhA, dhB and Trp are acid labile and are not detected by acid hydrolysis and OPA derivatization (Sahl et al., 1985, Antimicrob. Agents Chemother. 27:836–840), and Pro cannot be quantified by OPA derivatization.

According to Meyer et al. (1994, supra), the detection of a SEC signal (residues 5, 16, 19 and 21) during Edman degradation after ethanethiol treatment indicates the presence of a dhA residue. When this SEC signal is accompanied by a DSER signal (residues 3, 7, 11), it indicates the presence of a lanthionine residue. At cycles 16, 19 and 21, the DSER signal was not observed. These positions would correspond to a dhA residue. However, the DSER signal is always very low (Meyer et al., 1994, supra). It is possible that, as cycles 16, 19 and 21 are at the end of the sequence, the corresponding DSER signal is undetectable. Furthermore, if we compare the molecule of B-Ny266 with closely similar substances such as epidermin (staphylococcin 1580) and gallidermin (FIG. 1), position 16–21 is occupied by a lanthionine. This would also be in accordance with the results of the amino acid analysis, in which we detected 3 Lan/BM-Lan (Table 2). It can thus be hypothesized that these residues are Lan 3-7, BM-Lan 8-11 and Lan 16-21. The SEC signal detected at position 19 indicates a dhA in the molecule. This dhA could well result from breakage of a link with the S-(2-aminovinyl)-D-cysteine residue, leaving a dhA in position 19 and S-(2-aminovinyl) in the terminal position (which was not detected during the sequence analysis). Although it was not detected, this C-terminal aminovinyl-cysteinyl residue can be assumed from the comparison of the molecular masses obtained by mass spectroscopy analysis (2270.29±0.21 Da) and the total mass obtained from the addition of all the residues calculated from the amino acid sequence (2196.55 Da) (Table 2). The difference between the two masses (73.74±0.21 Da) agrees well with the molecular mass of a S-(2-aminovinyl) residue (73.12 Da). This assumption would again correspond to the known structures of epidermin and gallidermin (FIG. 1).

The signals corresponding to BMSEC indicate the presence of an Abu or a dhB (Meyer et al., 1994, supra). These signals are observed for residues 8 and 14 during the sequencing. By analogy with the molecules of epidermin and gallidermin, Abu was assigned for residue 8 and dhB for residue 14.

If the same mode of posttranslational modification for mutacin B-Ny266 as for other lantibiotics (Jack et al., 1995, Trends Biotechnol. 13:269–278.; Jung, 1991, in: Nisin and Novel Lantibiotics., Jung et al., Eds., pp. 1–34. ESCOM Science, Leiden) is hypothesized, the pro-B-Ny266 would thus have the following sequence: F-K-S-W-S-F-C-T-P-G-C-A-K-T-G-S-F-N-S-Y-C-C (SEQ ID NO:1). Confirmation of this sequence awaits the cloning and sequencing of the corresponding gene.

Nevertheless, it is very likely that the primary sequence of the pro-protein and that of its modified derivative are correct based on the data presented, the comparison of those sequences with other lantibiotics and their shared biological activities.

According to the results presented, mutacin B-Ny266 differs from epidermin and gallidermin in positions 1, 2, 4, 5 and 6 and could thus be regarded as a type A lantibiotic (FIG. 1 and Table 3). It is surprising that similar lantibiotics are produced by different bacterial genera. Epidermin and gallidermin are produced by staphylococci (*S. epidermidis* and *S. gallinarum* respectively) while mutacin B-Ny266 is produce by a streptococci (*S. mutans*). The Lan3-7, which is a common structure among group A lantibiotics (Jack et al., 1995, Microbiol. Rev. 59:171–200), is also present in mutacin B-Ny266. The Lys2 is also found in subtilin and streptococcin (SA-FF22). The importance of this position for the characteristics of the molecule have so far not been studied. The sequence F1-K2-Lan3 can be found in inverted form as F5-K4-Lan3 in epidermin/staphylococcin 1580 and gallidermin. The significance of this observation is not so clear at the moment, but it could point toward a common origin for these three lantibiotics.

Mutacin B-Ny266 possesses a dhA residue in position 5. This dhA5 was found to be important for the activity and stability of Nisin (Rollema et al., 1995, Appl. Environ. Microbiol. 61:2873–2878), and for the sporicidal activity of Nisin (Chan et al., 1996, Appl. Environ. Microbiol. 62:2966–2969) and subtilin (Liu et al., 1993, Appl. Environ. Microbiol. 59:648–651). A similar implication of the dhA5 residue in mutacin B-Ny266 activity is therefore likely and should therefore be formally tested. Position 6 of epidermin and gallidermin seems to be implicated in antibacterial activity and resistance to trypsin (Ottenwälder et al., 1995, Appl. Environ. Microbiol. 61:3894–3903). While this position is occupied by I and L residues in epidermin and gallidermin, respectively, an F6 residue is found in mutacin B-Ny266, as for streptococcin A-FF22 (Jack et al., 1991, in: Nisin and Novel Lantibiotics., Jung et al., Eds., pp. 171–179. ESCOM Science, Leiden) Mutacin B-Ny266, epidermin, gallidermin and SA-FF22 must be compared with respect to their resistance to trypsin and their spectrum of action to assess the structure/function relationship of this residue.

EXAMPLE 1

The sensitivity of multi-drug resistant strains to mutacin B-Ny266 purified to homogeneity was assessed. In parallel the sensitivity of these strains to nisin was determined.

Table 3 shows that mutacin B-Ny266 is as potent a bactericidal agent against the tested multi-drug resistant strains as the very well known and used Nisin. Once again, this result demonstrates the utility of this newly identified mutacin.

Furthermore, Table 3 shows that the homogeneously purified mutacin B-Ny266 possesses a potent antibacterial activity. This strongly suggests that mutacin B-Ny266 is responsible for the bactericidal activity demonstrated by strain B-Ny266 (Morency et al., 1995, Can. J. Microbiol. 41:826–831).

It has now also been discovered that mutacin B-Ny266 inhibits the growth of *Neisseria subflava, Clostridium bifermentants,* and *Bacillus cereus.* In addition, mutacin B-Ny266 was shown to inhibit *Flavobacterium capsulatum,* a Gram-negative strain. It therefore appears that the sensitivity of bacterial strains to mutacin B-Ny266 is not limited to Gram-positive strains.

Conclusion

Our invention presents the first complete sequence of a lantibiotic produced by *Streptococcus mutans.* The inhibitory substance produced by *S. mutans* Ny266 was purified to homogeneity and its proposed modified primary amino acid sequence was determined as: F-K-A-W-U-F-A-Abu-P-G-A-A-K-O-G-A-F-N-U-Y-A-SADC (underlined residues participate in lanthionine or b-methyllanthionine bridges). Mutacin B-Ny266 is resistant to a temperature of 100° C. for 30 min. and to many enzymes. Its activity is destroyed by a treatment at 121° C. for 30 min. and by the enzymes alpha-chymotrypsin, papain, pronase E, proteinase K and trypsin. It has a polarity of 8.067 as determined by its elution with 33.3% acetonitrile from a RP-HPLC $C_{18}$ chromatography column. The electrospray mass spectroscopy analysis yielded a molecular mass of 2270.29±0.21 daltons. Mutacin B-Ny266 is a type A lantibiotic. It substantially differs from other type A lantibiotics by its amino acid sequence but is closely related to Epidermin and Gallidermin.

Although the present invention has been described hereinabove by way of preferred embodiments thereof, it can be modified, without departing from the spirit and nature of the subject invention as defined in the appended claims.

What is claimed is:

1. A method for the prophylaxis or treatment of a bacterial infection in an animal, comprising the step of administering a therapeutically effective amount of a pharmaceutical composition which comprises an effective amount of an isolated mutacin B-Ny266 polypeptide, comprising the amino acid sequence as set forth in SEQ ID NO:4 wherein residues at positions 3, 7, 8, 11, 16, 19 and 21 thereof are capable of participating in lanthionine or b-methyllanthionine bridges, and a pharmaceutically acceptable carrier or excipient.

2. The method of claim 1, wherein said B-Ny266 polypeptide has the structure according to FIG. 1.

3. The method of claim 1, wherein said animal is a human patient, and said bacterial infection is caused by a Gram positive strain selected from the group consisting of Actinobacilli, Bacillus sp., Clostridium sp., Corynebacteria, Enterococci, *Listeria monocytogenes, Flavobacterium capsulatum, Mycobacterium phlei,* Staphylococci, Streptococci, and Propionibacter sp.

4. The method of claim 2, wherein said animal is a human patient, and said bacterial infection is caused by a Gram positive strain selected from the group consisting of Actinobacilli, Bacillus sp., Clostridium sp., Corynebacteria, Enterococci, *Listeria monocytogenes, Mycobacterium phlei, Flavobacterium capsulatum*, Staphylococci, Streptococci, and Propionibacter sp.

5. A method for inhibiting sensitive bacteria comprising: exposing said bacteria to an inhibitory amount of an isolated mutacin B-Ny266 polypeptide comprising the amino acid sequence of pro-B-Ny266 as set forth in SEQ ID NO:1.

6. A method for inhibiting sensitive bacteria comprising: exposing said bacteria to an inhibitory amount of an isolated mutacin B-Ny266 polypeptide comprising the amino acid sequence of B-Ny266 as set forth in SEQ ID NO:4, wherein residues at positions 3, 7, 8, 11, 16, 19 and 21 thereof are capable of participating in lanthionine or b-methyllanthionine bridges.

7. The method of claim 6, wherein said B-Ny266 polypeptide has the sequence as set forth in SEQ ID NO:4, wherein residues at positions 3, 7, 8, 11, 16, 19 and 21 thereof are capable of participating in lanthionine or b-methyllanthionine bridges.

8. The method of claim 7, wherein said B-Ny266 polypeptide has the structure according to FIG. 1.

9. A method for inhibiting sensitive bacteria comprising: exposing said bacteria to an inhibitory amount of a substantially pure preparation of mutacin from *Streptococcus mutans,* having a structure according to FIG. 1.

10. The method of claim 9, wherein said mutacin comprises the amino acid sequence as set forth in SEQ ID NO:4, wherein residues at positions 3, 7, 8, 11, 16, 19 and 21 thereof participate in lanthionine or b-methyllanthionine bridges.

11. The method of claim 10, wherein said mutacin has the amino acid sequence as set forth in SEQ ID NO:4, wherein residues at positions 3, 7, 8, 11, 16, 19 and 21 thereof participate in lanthionine or b-methyllanthionine bridges.

12. The method of claim 1, wherein said animal is a human patient, and said bacterial infection is caused by a Gram negative strain.

13. The method of claim 12, wherein said Gram negative strain is selected from a Neisseria strain or a *Flavobacterium capsulum* strain.

14. The method of claim 2, wherein said animal is a human patient, and said bacterial infection is caused by a Gram negative strain.

15. The method of claim 14, wherein said Gram negative strain is selected from a Neisseria strain or a *Flavobacterium capsulum* strain.

* * * * *

SEQUENCE LISTING

<160> NUMBER OF SEQ ID NOS: 5

<210> SEQ ID NO 1
<211> LENGTH: 22
<212> TYPE: PRT
<213> ORGANISM: Streptococcus mutans

<400> SEQUENCE: 1

Phe Lys Ser Trp Ser Phe Cys Thr Pro Gly Cys Ala Lys Thr Gly Ser
 1               5                  10                  15

Phe Asn Ser Tyr Cys Cys
            20

<210> SEQ ID NO 2
<211> LENGTH: 21
<212> TYPE: PRT
<213> ORGANISM: Streptococcus mutans
<220> FEATURE:
<221> NAME/KEY: SITE
<222> LOCATION: (3)
<223> OTHER INFORMATION: Xaa represents 2,3-didehydroalanine (dhA or U)
<220> FEATURE:
<221> NAME/KEY: SITE
<222> LOCATION: (5)
<223> OTHER INFORMATION: Xaa represents 2,3-didehydroalanine (dhA or U)
<220> FEATURE:
<221> NAME/KEY: SITE
<222> LOCATION: (8)
<223> OTHER INFORMATION: Xaa represents 2-aminobutyric acid (Abu)
<220> FEATURE:
<221> NAME/KEY: SITE
<222> LOCATION: (14)
<223> OTHER INFORMATION: Xaa represents 2,3-didehydrobutyrine (dhB or O)
<220> FEATURE:
<221> NAME/KEY: SITE
<222> LOCATION: (16)
<223> OTHER INFORMATION: Xaa represents 2,3-didehydroalanine (dhA or U)
<220> FEATURE:
<221> NAME/KEY: SITE
<222> LOCATION: (19)
<223> OTHER INFORMATION: Xaa represents 2,3-didehydroalanine (dhA or U)

<400> SEQUENCE: 2

Phe Lys Xaa Trp Xaa Phe Cys Xaa Pro Gly Cys Ala Lys Xaa Gly Xaa
 1               5                  10                  15

Phe Asn Xaa Tyr Cys
            20

<210> SEQ ID NO 3
<211> LENGTH: 22
<212> TYPE: PRT
<213> ORGANISM: Streptococcus mutans
<220> FEATURE:
<221> NAME/KEY: SITE
<222> LOCATION: (3)
<223> OTHER INFORMATION: Xaa represents 2,3-didehydroalanine (dhA or U)
<220> FEATURE:
<221> NAME/KEY: SITE
<222> LOCATION: (5)
<223> OTHER INFORMATION: Xaa represents 2,3-didehydroalanine (dhA or U)
<220> FEATURE:
<221> NAME/KEY: SITE
<222> LOCATION: (8)
<223> OTHER INFORMATION: Xaa represents 2-aminobutyric acid (Abu)
<220> FEATURE:
<221> NAME/KEY: SITE
<222> LOCATION: (14)
<223> OTHER INFORMATION: Xaa represents 2,3-didehydrobutyrine (dhA or U)
<220> FEATURE:
<221> NAME/KEY: SITE

```
<222> LOCATION: (16)
<223> OTHER INFORMATION: Xaa represents 2,3-didehydroalanine (dhA or U)
<220> FEATURE:
<221> NAME/KEY: SITE
<222> LOCATION: (19)
<223> OTHER INFORMATION: Xaa represents 2,3-didehydroalanine (dhA or U)

<400> SEQUENCE: 3

Phe Lys Xaa Trp Xaa Phe Cys Xaa Pro Gly Cys Ala Lys Xaa Gly Xaa
 1               5                  10                  15

Phe Asn Xaa Tyr Cys Cys
            20

<210> SEQ ID NO 4
<211> LENGTH: 21
<212> TYPE: PRT
<213> ORGANISM: Streptococcus mutans
<220> FEATURE:
<221> NAME/KEY: SITE
<222> LOCATION: (3)
<223> OTHER INFORMATION: Xaa represents 2,3-didehydroalanine (dhA or U)
<220> FEATURE:
<221> NAME/KEY: SITE
<222> LOCATION: (5)
<223> OTHER INFORMATION: Xaa represents 2,3-didehydroalanine (dhA or U)
<220> FEATURE:
<221> NAME/KEY: SITE
<222> LOCATION: (8)
<223> OTHER INFORMATION: Xaa represents 2-aminobutyric acid (Abu)
<220> FEATURE:
<221> NAME/KEY: SITE
<222> LOCATION: (14)
<223> OTHER INFORMATION: Xaa represents 2,3-didehydrobutyrine (dhB or O)
<220> FEATURE:
<221> NAME/KEY: SITE
<222> LOCATION: (16)
<223> OTHER INFORMATION: Xaa represents 2,3-didehydroalanine (dhA or U)
<220> FEATURE:
<221> NAME/KEY: SITE
<222> LOCATION: (19)
<223> OTHER INFORMATION: Xaa represents 2,3-didehydroalanine (dhA or U)
<220> FEATURE:
<221> NAME/KEY: SITE
<222> LOCATION: (21)
<223> OTHER INFORMATION: Xaa represents 2,3-didehydroalanine (dhA or U)

<400> SEQUENCE: 4

Phe Lys Xaa Trp Xaa Phe Cys Xaa Pro Gly Cys Ala Lys Xaa Gly Xaa
 1               5                  10                  15

Phe Asn Xaa Tyr Xaa
            20

<210> SEQ ID NO 5
<211> LENGTH: 22
<212> TYPE: PRT
<213> ORGANISM: Streptococcus mutans
<220> FEATURE:
<221> NAME/KEY: SITE
<222> LOCATION: (3)
<223> OTHER INFORMATION: Xaa represents 2,3-didehydroalanine (dhA or U)
<220> FEATURE:
<221> NAME/KEY: SITE
<222> LOCATION: (5)
<223> OTHER INFORMATION: Xaa represents 2,3-didehydroalanine (dhA or U)
<220> FEATURE:
<221> NAME/KEY: SITE
<222> LOCATION: (8)
<223> OTHER INFORMATION: Xaa represents 2-aminobutyric (Abu)
<220> FEATURE:
<221> NAME/KEY: SITE
<222> LOCATION: (14)
<223> OTHER INFORMATION: Xaa represents 2,3-didehydrobutyrine (dhB or O)
<220> FEATURE:
```

-continued

```
<221> NAME/KEY: SITE
<222> LOCATION: (16)
<223> OTHER INFORMATION: Xaa represents 2,3-didehydroalanine (dhA or U)
<220> FEATURE:
<221> NAME/KEY: SITE
<222> LOCATION: (19)
<223> OTHER INFORMATION: Xaa represents 2,3-didehydroalanine (dhA or U)
<220> FEATURE:
<221> NAME/KEY: SITE
<222> LOCATION: (21)
<223> OTHER INFORMATION: Xaa represents 2,3-didehydroalanine (dhA or U)
<220> FEATURE:
<221> NAME/KEY: SITE
<222> LOCATION: (22)
<223> OTHER INFORMATION: Xaa represents S-(2-aminovinyl)-D-cysteine
      (SADC)

<400> SEQUENCE: 5

Phe Lys Xaa Trp Xaa Phe Cys Xaa Pro Gly Cys Ala Lys Xaa Gly Xaa
  1               5                  10                  15

Phe Asn Xaa Tyr Xaa Xaa
             20
```